(12) United States Patent
Umasuthan et al.

(10) Patent No.: US 9,101,267 B2
(45) Date of Patent: Aug. 11, 2015

(54) METHOD OF REAL-TIME TRACKING OF MOVING/FLEXIBLE SURFACES

(71) Applicant: MACDONALD DETTWILER & ASSOCIATES, Brampton (CA)

(72) Inventors: Manickam Umasuthan, Mississauga (BF); Raja Mukherji, Brampton (CA); Limin Shang, Maple (CA)

(73) Assignee: MACDONALD, DETTWILER AND ASSOCIATES INC., Brampton, ON (CA)

( * ) Notice: Subject to any disclaimer, the term of this patent is extended or adjusted under 35 U.S.C. 154(b) by 0 days.

(21) Appl. No.: 14/221,085

(22) Filed: Mar. 20, 2014

(65) Prior Publication Data

US 2014/0206935 A1 Jul. 24, 2014

Related U.S. Application Data

(62) Division of application No. 13/678,162, filed on Nov. 15, 2012, now Pat. No. 8,693,730.

(60) Provisional application No. 61/560,072, filed on Nov. 15, 2011, provisional application No. 61/723,994, filed on Nov. 8, 2012.

(51) Int. Cl.
*G06K 9/00* (2006.01)
*A61B 1/00* (2006.01)
(Continued)

(52) U.S. Cl.
CPC ......... *A61B 1/00149* (2013.01); *A61B 1/00193* (2013.01); *A61B 1/06* (2013.01);
(Continued)

(58) Field of Classification Search
CPC .... A61B 19/2203; A61B 19/20; A61B 19/50; A61B 1/00149; A61B 1/00193; A61B 1/06; G06T 7/2086

USPC .......... 382/103, 128, 130, 131, 132; 128/922; 600/1, 11, 179, 178, 103, 129, 228; 348/169; 606/130, 139
See application file for complete search history.

(56) References Cited

U.S. PATENT DOCUMENTS 8,073,528 B2 12/2011 Zhao et al.
8,147,503 B2 4/2012 Zhao et al.
(Continued)

FOREIGN PATENT DOCUMENTS

CA 2252409 10/1997
CA 2762038 12/2010
WO 9607144 3/1996

OTHER PUBLICATIONS

Kasper Claes, Herman Bruyninckx. Endostitch automation using 2D and 3D vision. Department of Mechanical Engineering, Katholieke Universiteit Leuven, Belgium, 2006.
(Continued)

*Primary Examiner* — Ali Bayat
(74) *Attorney, Agent, or Firm* — Lynn C. Schumacher; Hill & Schumacher (57) ABSTRACT

The present invention provides a method for real-time tracking of moving flexible surfaces and an image guided surgical robotic system using this tracking method. A vision system acquires an image of the moving flexible surface and identifies and tracks visual features at different times. The method involves computing both rigid and stretching transformations based on the changing positions of the visual features which are then used to track any area of interest on the moving flexible surface as it evolves over time. A robotic surgical system using this real-time tracking is disclosed.

11 Claims, 3 Drawing Sheets

(51) Int. Cl.
*A61B 19/00* (2006.01)
*A61B 1/06* (2006.01)
*G06T 7/20* (2006.01)

(52) U.S. Cl.
CPC ............ *A61B 19/20* (2013.01); *A61B 19/2203* (2013.01); *A61B 19/50* (2013.01); *G06T 7/2086* (2013.01); *A61B 2019/505* (2013.01); *A61B 2019/5227* (2013.01); *A61B 2019/5265* (2013.01)

(56) References Cited

U.S. PATENT DOCUMENTS

| | | | |
|---|---|---|---|
| 2003/0071194 | A1 | 4/2003 | Mueller et al. |
| 2009/0088897 | A1* | 4/2009 | Zhao et al. ............... 700/250 |
| 2012/0020547 | A1* | 1/2012 | Zhao et al. ............... 382/153 |
| 2012/0101370 | A1 | 4/2012 | Razzaque et al. |

OTHER PUBLICATIONS

Krupa A et al. Autonomous 3-D positioning of surgical instruments in robotized laparoscopic surgery using visual servoing. IEEE Transactions on Robotics and Automation, 19, 5 (2003), 842-853.

Mitsuhiro Hayashibe, Naoki Suzuki, Yoshihiko Nakamura. Laser-scan endoscope system for intraoperative geometry acquisition and surgical robot safety management. Medical Image Analysis, 10 (2006), 509-519.

Krupa Alexandre, Doignon Christophe, Gangloff Jacques, Mathelin Michel de, Soler Luc, Morel Guillaume. Towards Semi-autonomy in Laparoscopic Surgery through Vision and Force Feedback Control. In Experimental Robotics VII ( 2001), Springer-Verlag, London, UK, 189-198.

W. Eric L. Grimson, Ron Kikinis, Ferenc A. Jolesz, Peter McL. Black. Image Guided Surgery. Scientific American (Jun. 1999), 62-69.

Takayuki Osa, Christoph Staub, Alois Knoll. Framework of Automatic Robot Surgery System using Visual Servoing. In The 2010 IEEE/RSJ International Conference on Intelligent Robots and Systems (Taiwan 2010), 1837-1842.

Simon DiMaio et al. Challenges in image-guided therapy system design. NeuroImage, 37 (2007), S144-S151.

Danail Stoyanov, Ara Darzi, Guang Zhong Yang. A practical approach towards accurate dense 3D depth recovery for robotic laparoscopic surgery. Computer Aided Surgery, 10, 4 (Jul. 2005), 199-208.

Baumhauer M, Feuerstein M, Menzer HP, Rassweiler J. Navigation in endoscopic soft tissue surgery: perspectives and limitations. Journal of EndoUrology, 22, 4 (2008), 751-766.

Kristofer R. Wagner, Thomas W. Jarrett, Jason D. Engel. Robotic-Assisted Pyeloplasty. In Robotic Surgery. McGraw-Hill Ryerson Ltd, 2009.

Krupa A et al. Autonomous retrieval and positioning of surgical instruments in robotized laparoscopic surgery using visual servoing and laser pointers. In Proceedings. ICRA '02. IEEE International Conference on Robotics and Automation, 2002. ( 2002), 3769-3774 vol. 4.

Martin Groeger, Klaus Arbter, Gerd Hirzinger. Motion Tracking for Minimally Invasive Robotic Surgery. In Medical Robotics. 2008.

Matsuoka Yoky, Robert D. Howe. Robotics for Surgery. Annu, Rev. Biomed. Eng (1999), 211-240.

Nakamura Mitsuhiro, Hayashibe Yoshihiko. Laser-Pointing Endoscope System for Intra-Operative 3D Geometric Registration. In Proceedings of the 2001 IEEE International Conference on Robotics 8 Automation (Seoul, Korea 2001), 1543-1548.

Kang H, Wen JT. Robotic Assistants Aid Surgeons During Minimally Invasive Procedures. IEEE Engineering in Medicine and Biology (Jan./Feb. 2001), 94-104.

PCT International Search Report dated Mar. 4, 2013.

* cited by examiner

FIGURE 2

METHOD OF REAL-TIME TRACKING OF MOVING/FLEXIBLE SURFACES

CROSS REFERENCE TO RELATED U.S. PATENT APPLICATION

This patent application is a divisional application of U.S. patent application Ser. No. 13/678,162, entitled "METHOD OF REAL-TIME TRACKING OF MOVING/FLEXIBLE SURFACES", filed on Nov. 13, 2012, which relates to and claims the priority benefit from, U.S. provisional patent application Ser. No. 61/560,072 filed on Nov. 15, 2011, entitled SHARED CONTROL IMAGE GUIDED SURGICAL SYSTEM AND METHOD, filed in English, and U.S. provisional patent application 61/723,994, filed Nov. 8, 2012, filed in English, all of which are incorporated herein in their entirety by reference.

FIELD

The present invention relates to a method for real-time tracking of moving flexible surfaces and an image guided surgical robotic system using this tracking method.

BACKGROUND

Before robotically assisted surgery can become widely available, a vision system that is capable of real-time tracking of moving tissue such as deformable lumens is required. The main limitation of the known techniques is that the type of deformation function needs to be physically modeled accurately in order for the tracking to work. This is because the previous deformable tracking techniques used to track the surface employs these physical models whose parameters are identified using optimization techniques based on observations of the flexible surface. However many times these physical models are not validated with real tissues (in medical applications). This method also fails when there is occlusion by other objects in the scene and in cases where the underlying surface folds, as is the case with irregularly shaped tissue which may fold as it is being manipulated.

It would be very advantageous to provide a real-time tracking method able to track moving surfaces.

SUMMARY OF THE INVENTION

The present invention provides a method for real-time tracking of moving flexible surfaces and an image guided surgical robotic system using this tracking method. A vision system acquires an image of the moving flexible surface and identifies and tracks visual features at different times. The method involves computing both rigid and stretching transformations based on the changing positions of the visual features which are then used to track any area of interest on the moving flexible surface as it evolves over time. A robotic surgical system using this real-time tracking is disclosed.

An embodiment disclosed herein provides a method on a computer for real time tracking of a moving flexible surfaces, comprising:

a) synchronously acquiring left and right image frames from left and right camera members of a stereo camera, of a region of interest on a moving flexible surface at a time K;

b) computing, from the left and right image frames 3D point cloud data in a coordinate frame of the stereo camera at the time K;

c) fitting a parametric surface to the 3D point cloud at the time K;

d) extracting a location of at least three features of interest in the left image frame at the time K in 2D pixel coordinates, extracting a location of each at least three feature of interest in the right image frame at the time K in 2D pixel coordinates, storing the 2D pixel coordinates of the locations of the features of interest in the left and right image frames at the time K in a vision processor memory storage;

e) computing, using the stored 2D pixel coordinates of the locations of the features of interest in the left and right image frames at the time K, a 3D location of the features of interest at the time K in a coordinate frame of the camera and storing the 3D locations in the vision processor memory storage;

f) mapping the 3D location of the features of interest onto the parametric surface at time K and storing the parametric surface with mapped 3D locations in the vision processor memory storage;

g) retrieving from the vision processor memory storage 3D locations of the features of interest from previous left and right image frames synchronously taken at a time K−1;

h) computing a best fit rigid transform using the retrieved 3D locations of the features of interest at time K−1 and the 3D locations of the features at time K;

i) retrieving from the vision processor memory storage a parametric surface with mapped 3D locations at time K−1, applying the rigid transformation to the retrieved parametric surface with mapped 3D locations at time K−1 to obtain an intermediate parametric surface with mapped 3D locations;

j) matching the 3D locations of features of interest on the intermediate parametric surface at time K−1 to the same corresponding 3D locations on the stored parametric surface at time K and from the correspondences computing a stretching transformation; and k) using the rigid and stretching transformations to calculate at time K a location of any region on the moving flexible surface based on a location of the same region on the moving flexible surface at time K−1 stored in the vision processor memory storage.

There is also disclosed a method on a computer for real time tracking of a moving flexible surface, comprising:

a) acquiring at time K, using a sensor, a 3D point cloud by scanning a moving flexible surface;

b) fitting a parametric surface to the 3D point cloud at the time K;

c) computing and labeling at least three 3D features from the 3D point cloud at the time K in a coordinate frame of the sensor and storing the 3D locations of the at least three 3D features in a vision processor memory storage;

f) mapping the 3D location of the 3D features of interest onto the parametric surface at time K and storing the parametric surface with mapped 3D locations in the vision processor memory storage;

g) retrieving from the vision processor memory storage 3D locations of the features of interest from previous left and right image frames synchronously taken at a time K−1;

h) computing a best fit rigid transform using the retrieved 3D locations of the features of interest at time K−1 and the 3D locations of the features at time K;

i) retrieving from the vision processor memory storage a parametric surface with mapped 3D locations at time K−1, applying the rigid transformation to the retrieved parametric surface with mapped 3D locations at time K−1 to obtain an intermediate parametric surface with mapped 3D locations;

j) matching the 3D locations of features of interest on the intermediate parametric surface at time K−1 to the same corresponding 3D locations on the stored parametric surface at time K and from the correspondences computing a stretching transformation; and k) using the rigid and stretching transformations to calculate at time K a location of any region on the deformable surface based on a location of the same region on the deformable surface at time K−1 stored in the vision processor memory storage.

There is also disclosed a vision system for real-time tracking of moving and flexible surfaces, comprising:

a) a 3D sensor for acquiring 3D images of a region of a moving flexible surface producing a 3D point cloud of the region of moving flexible surface, b) a vision processor connected to the 3D sensor, the vision processor programmed with instructions for computing, in real time, a current location of the region of moving flexible surface based on a current 3D point cloud of the region of moving flexible surface and a previous location of the region of moving flexible surface based on a previous 3D point cloud;

c) a computer controller connected to the vision processor, the computer controller including a visual display for displaying images of a region of the moving flexible surface;

g) the computer controller being programmed to pass one or more designated positions on the moving flexible surface to the vision processor, and wherein the vision processor is programmed to continuously track the one or more designated surgical positions on the moving flexible surface to provide updated positions of the one or more designated positions.

There is also disclosed a vision system for real-time tracking of moving and flexible surfaces, comprising:

a) a 3D sensor for acquiring 3D images of a region of a moving flexible surface producing a 3D point cloud of the region of moving flexible surface, b) a vision processor connected to the 3D sensor, the vision processor programmed with instructions for computing, in real time, a current location of the region of moving flexible surface based on a current 3D point cloud of the region of moving flexible surface and a previous location of the region of moving flexible surface based on a previous 3D point cloud;

c) a computer controller connected to the vision processor, the computer controller including a visual display for displaying images of a region of the moving flexible surface;

g) the computer controller being programmed to pass one or more designated positions on the moving flexible surface to the vision processor, and wherein the vision processor is programmed to continuously track the one or more designated surgical positions on the moving flexible surface to provide updated positions of the one or more designated positions.

There is also provided an image-guided surgical system for performing procedures on deformable and/or moving sections of tissue, comprising:

a) a stereo endoscope for acquiring images of a region of moving tissue and a surgical tool tip being used in the region of tissue, and a light source for illuminating the region of moving tissue and the surgical tool;

b) a vision processor connected to the stereo endoscope and the light source, the visional processor programmed with instructions for analyzing images from the stereo endoscope and computing, in real time, a current location of the region of moving tissue based on a current image of the region of moving tissue and a previous location of the region of moving tissue;

c) a computer controller connected to the vision processor, the computer controller including a visual display for displaying images of a region of tissue being operated on in which the region of moving tissue is located;

d) a robot controller connected to the computer controller;

e) at least one surgical robot connected to the robot controller;

f) a surgical tool releasibly grippable by the robot, the surgical tool including the surgical tool tip;

g) the computer controller being programmed to pass one or more designated surgical positions being acted on by the surgical tool tip on the region of moving tissue to the vision processor, and wherein an operator initiates a surgical procedure by instructing the computer controller to command the robot to activate the surgical tool tip to proceed to a first of the one or more designated surgical positions, and wherein the vision processor is programmed to continuously track the one or more designated surgical positions on the moving tissue to provide updated positions of the one or more designated positions, and communicate these updated positions to the robot controller for tracking and to the computer controller for display to the operator, and wherein the computer controller is programmed to command the surgical robot to proceed to each designated position and perform a surgical procedure in a preselected order from the first designated position point to a final designated position.

There is also provided an article of manufacture, which comprises a computer readable medium having stored thereon a computer program for real time tracking of a deformable surface, comprising:

a) a first code segment which, when executed on a computer, analyses left and right image frames from left and right camera members of a stereo camera of a region of interest on a deformable surface at a time K and computes, from the left and right image frames, 3D point cloud data in a coordinate frame of the stereo camera at the time K, and fits a parametric surface to the 3D point cloud at the time K;

b) a second code segment which, when executed on a computer, extracts a location of at least three features of interest in the left image frame at the time K in 2D pixel coordinates, extracts a location of each at least three feature of interest in the right image frame at the time K in 2D pixel coordinates, and stores the 2D pixel coordinates of the locations of the features of interest in the left and right image frames at the time K in a storage device;

c) a third code segment which, when executed on a computer, computes, using the stored 2D pixel coordinates of the locations of the features of interest in the left and right image frames at the time K, a 3D location of the features of interest at the time K in a coordinate frame of the camera and storing the 3D locations in the storage device;

d) a fourth code segment which, when executed on a computer, maps the 3D location of the features of interest onto the parametric surface at time K and stores the parametric surface with mapped 3D locations in the storage device;

e) a fifth code segment which, when executed on a computer, retrieves from the storage device 3D locations of the features of interest from previous left and right image frames synchronously taken at a time K−1 and computes a best fit rigid transform using the retrieved 3D locations of the features of interest at time K−1 and the 3D locations of the features at time K;

f) a sixth code segment which, when executed on a computer, retrieves from the storage device a parametric surface with mapped 3D locations at time K−1, applies the rigid transformation to the retrieved parametric surface with mapped 3D locations at time K−1 to obtain an intermediate parametric surface with mapped 3D locations and matches the 3D locations of features of interest on the intermediate parametric surface at time K−1 to the same corresponding 3D locations on the stored parametric surface at time K and from the correspondences computes a stretching transformation; and g) a seventh code segment which, when executed on a computer, uses the rigid and stretching transformations to calculate at time K a location of any region on the deformable surface based on a location of the same region on the deformable surface at time K−1 stored in the storage device.

BRIEF DESCRIPTION OF THE DRAWINGS

The invention will be more fully understood from the following detailed description thereof taken in connection with the accompanying drawings, which form part of this application, and in which.

DETAILED DESCRIPTION

Generally speaking, the systems described herein are directed to a method for real-time tracking of deformable surfaces such as, but not limited to, moving and/or deformable tissue such as lumen including blood vessels etc. (in other words a surface which is changing shape over time) and the use of such real-time tracking method for robotic assisted surgery.

As used herein, the phrase "real time" refers to the characteristic of a process that occurs as part of a larger system. This characteristic is such that the total time for reaction and execution of the process is no more than a maximum allowable delay, in view of the larger system's operations. For example, a system for determining the position of a moving object that is intended to be a "real-time system" must be capable of determining the object's position quickly enough for it to represent a reasonable estimate of the object's instantaneous position, given that the object is moving at a certain rate of travel. In the present invention, a real-time process is generally considered to be one for which the positions and orientations of the suture points and a surgical tool is delivered to the surgical robot controller at a guaranteed pre-specified time interval.

As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a method for real time tracking of deformable and or moving surfaces and the use of such method for robotic assisted surgery.

Figure 1:
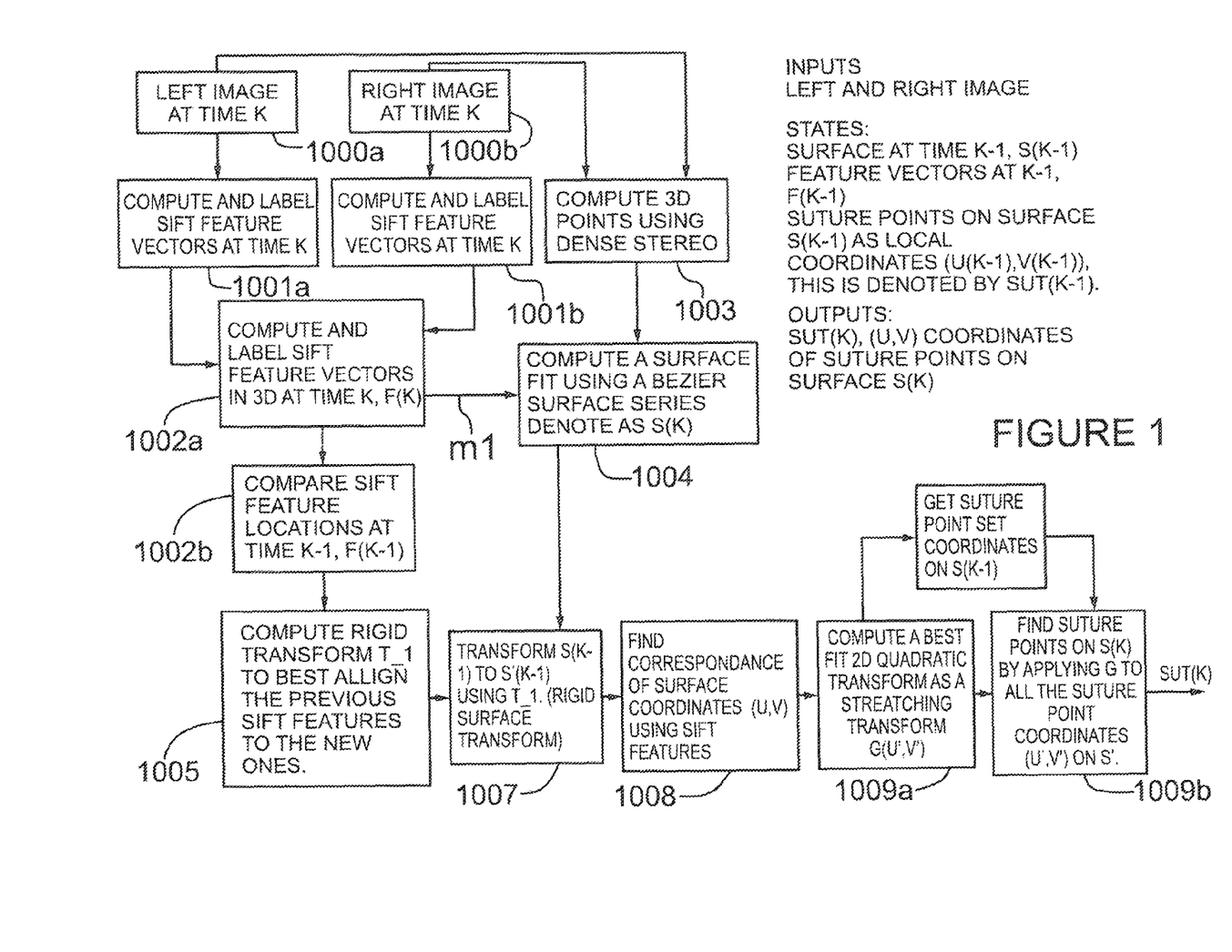
FIG. 1 shows a data flow/block diagram showing the steps for real-time tracking of moving and/or deforming surfaces using a stereo camera.

FIG. 1 shows a block diagram/flow chart of the method for real-time tracking of a moving and/or deformable surface. The method for real time tracking uses a stereo camera which has left and right camera sections. In steps 1000a and 1000b, images from the left and right stereo cameras are acquired synchronously.

In steps 1001a and 1001b the locations of a minimum of three features of interest are extracted from the left image frame at time K in 2D pixel coordinates, and the locations of these three features of interest are also extracted from the right image frame at time K in 2D pixel coordinates. The 2D pixel coordinates of these three locations in the left and right image frames at time K are stored in a computer memory.

It will be understood that the features of interest may be different types of features known to those familiar with imaging technology. For example, the features of interest may be SIFT (Scale Invariant Feature Transform, Lowe 1999) features which may be natural features on the surface, say, blood vessels, color contrasts, anything that causes a change in image intensity is considered a feature. Each scale invariant feature transform (SIFT) feature includes a descriptor vector including 64 elements. A minimum of three (3) features of interest are required but in practice many more are used, for example between 3 to about 100 features may be used but typically around 40 to about 60 features are used, since the larger number of features, the greater the computational load. For large number of extracted features, the computational load increases significantly during correspondence matching (discussed below). The number of features to use in correspondence matching is determined so as to provide real-time feedback of updated suture points to the surgical tool.

In addition to SIFT features, there are other feature descriptors that may be also be used for this application, including accelerated segment test (FAST) features. In this case, a learning algorithm is used to extract corner features in real time. A corner feature is defined as a pixel location where there are intensity changes in two dominant directions.

Another kind of feature that may be used are maximally stable extremal region (MSER) features. MSER is a robust blob detector. In this case, extremal regions or blobs in an image are detected by thresholding and the maximally stable extremeal regions are then extracted by comparing the nested extremal regions.

Another type of that may be used are Harris-Laplace features. In this case, the Laplacian operator is used to select the scale for Gaussian smoothing and then the Harris "cornerness" measure is used to detect corner points in the image.

In step 1002a, when the features of interest are SIFT features, a 3D location of the feature is computed by matching the SIFT features in the left and right images. The 3D coordinate of this feature is then stored in computer memory along with a feature vector that describes the feature characteristics. This is the feature descriptor.

In step 1003, 3D point cloud data in a coordinate frame of the stereo camera at the time K is computed from the left and right images. In one embodiment, the 3D point cloud data is computed from the left and right images by computing dense stereo disparity data using for example Hirschmuller's algorithm. However, any high performance dense stereo algorithm (Scharstein et al.) can also be used in step 1003. The dense stereo disparity data computed using the dense stereo algorithm is then converted into 3D point cloud data in the camera coordinate frame.

In an alternative method of computing the 3D point cloud data, the method involves first illuminating the region of interest with a structured light pattern and acquiring calibrated color images of the left and right image frames, followed by applying triangulation techniques to the left and right calibrated color images to compute the 3D point cloud data. More particularly, structured light illumination includes projecting either a color coded or monochrome coded illumination pattern onto the moving surface and computing the 3D coordinates using the method of triangulation. The optical centers of the coded structured illumination unit and the camera form the baseline. The step of triangulation includes intersecting the coded structured light plane with the optical ray which is obtained by connecting the camera optical center and a given point on the moving surface. Then the 3D coordinates of the given point on the moving plane is computed.

In step 1004, a parametric surface is fitted to the 3D point cloud data extracted in step 1003. An example of a parametric surface is a B-Spline surface. The number of basis functions for a given B-spline surface is specified by the degree of the B-spline which can be selected to best fit the underlying undulating surface.

Alternatively, instead of using a B-Spline surface, depending on the structure of the underlying 3D point cloud, other parametric representations may be used. For example, Bezier surfaces can also be used to obtain the parametric surface representation. Unlike B-Spline surfaces which are defined by piecewise basis functions in the parameter space, Bezier surfaces are defined by control points and Bernstein polynomial basis functions for the whole parameter space.

Alternatively, the step of fitting a parametric surface to the 3D point cloud at the time K includes fitting a non-uniform rational b-spline surface to the 3D point cloud. Non-uniform rational B-spline representation is similar to B-spline representation. However, the basis functions are weighted.

An alternative method for fitting a parametric surface to the 3D point cloud at the time K includes fitting a surface defined by selected radial basis functions to the 3D point cloud. Radial basis functions cover a broad class of surfaces including thin-plate splines and can be used in cases where there are irregular sampling of 3D points.

The computed 3D locations of the minimum of three features of interest are mapped onto the parametric surface at time K. This is denoted by the arrow labeled M step 1002*a* to step 1004. The parametric surface with 3D locations mapped thereon are then stored in the memory storage.

Step 1002*b* involves retrieving from the memory storage 3D locations of the features of interest from previous left and right image frames synchronously taken at a time K−1, and all of the previously stored feature descriptors for time K−1 are compared to the current feature descriptors at time K and matches are found. This then identifies the same features in frames K and the previous frame K−1.

In step 1005, a best fit rigid transform is estimated using the retrieved 3D locations of the features of interest at time K−1 and the 3D locations of the features of interest at time K. When SIFT features are used, the algorithm looks for conjugate SIFT features between the current (time K) and the previous frame (K−1). The number of features required must be greater than or equal to three and less than some limits which depend on computational constraints. A rigid transformation is a linear transformation which in general is characterized by a 4×4 matrix. A least squares algorithm is used to calculate the matrix coefficients.

Step 1007 includes retrieving from the memory storage a parametric surface with mapped 3D locations at time K−1, applying the rigid transformation to the retrieved parametric surface with mapped 3D locations at time K−1 to obtain an intermediate parametric surface with mapped 3D locations. This is followed by step 1008 which includes matching the 3D locations of the three features on the intermediate parametric surface at time K−1 to the same corresponding 3D locations on the stored parametric surface at time K and from the correspondences compute a 2D stretching transformation as in step 1009*a*. More particularly, we now have features on two 3D surfaces where the surfaces are roughly aligned after the rigid transformation in step 1007. Now using the same features, we compare the surface coordinates of the features. Knowing that two features are the same features with coordinates (u,v) and (u',v') we postulate that there exists a stretching transformation that relates these coordinates, which stretching transformation is computed in step 1009*a*.

In an embodiment, the stretching transformation may be a local, 2D nonlinear transformation applied to a parametric surface in 3D. It may also be a quadratic flexible transformation which has 16 independent parameters. By knowing the location of the features in both surfaces the unknown parameters are found using least square. In an embodiment the number of features may be between 40 to 60.

Once the rigid and stretching transformation has been computed, both may then be used using to calculate at time K a location of any region on the deformable surface based on a location of the same region on the deformable surface at time K−1 stored in the memory storage, shown in step 1009*b*.

The particular application illustrated in FIG. 1 in step 1009*b* is real time tracking of designated suture points when the method of FIG. 1 is real-time tracking of moving tissue and also in robotic assisted surgery, and the positions being tracked are surgeon specified suture points on moving tissue, such as but not limited to, deformable surfaces such as various lumen. It will however be appreciated that the present method illustrated in FIG. 1 has broad application to real time tracking of any moving, deformable surface, in any technological area.

There are several useful advantages of the process for real-time tracking of moving and/or deformable surfaces discussed above. First, when used in an image system for robotic assisted surgery using a surgical tool being manipulated by a medical robot, the feature detection and description (1001*a* and 1001*b*) steps keep track of those parts of the tissue surface which gets occluded due to the manipulation of the surgical tool. The surface fitting and stretching transformation estimation functions are performed locally which allows one to compute updated suture points in an efficient and robust manner.

The main limitation of the known techniques is that the type of deformation function needs to be physically modeled accurately in order for the tracking to work. This is because the previous deformable tracking techniques used to track the surface employs these physical models whose parameters are identified using optimization techniques based on observations of the flexible surface. However many times these physical models are not validated with real tissues (in medical applications). This method also fails when there is occlusion by other objects in the scene and in cases where the underlying surface folds.

Figure 2:
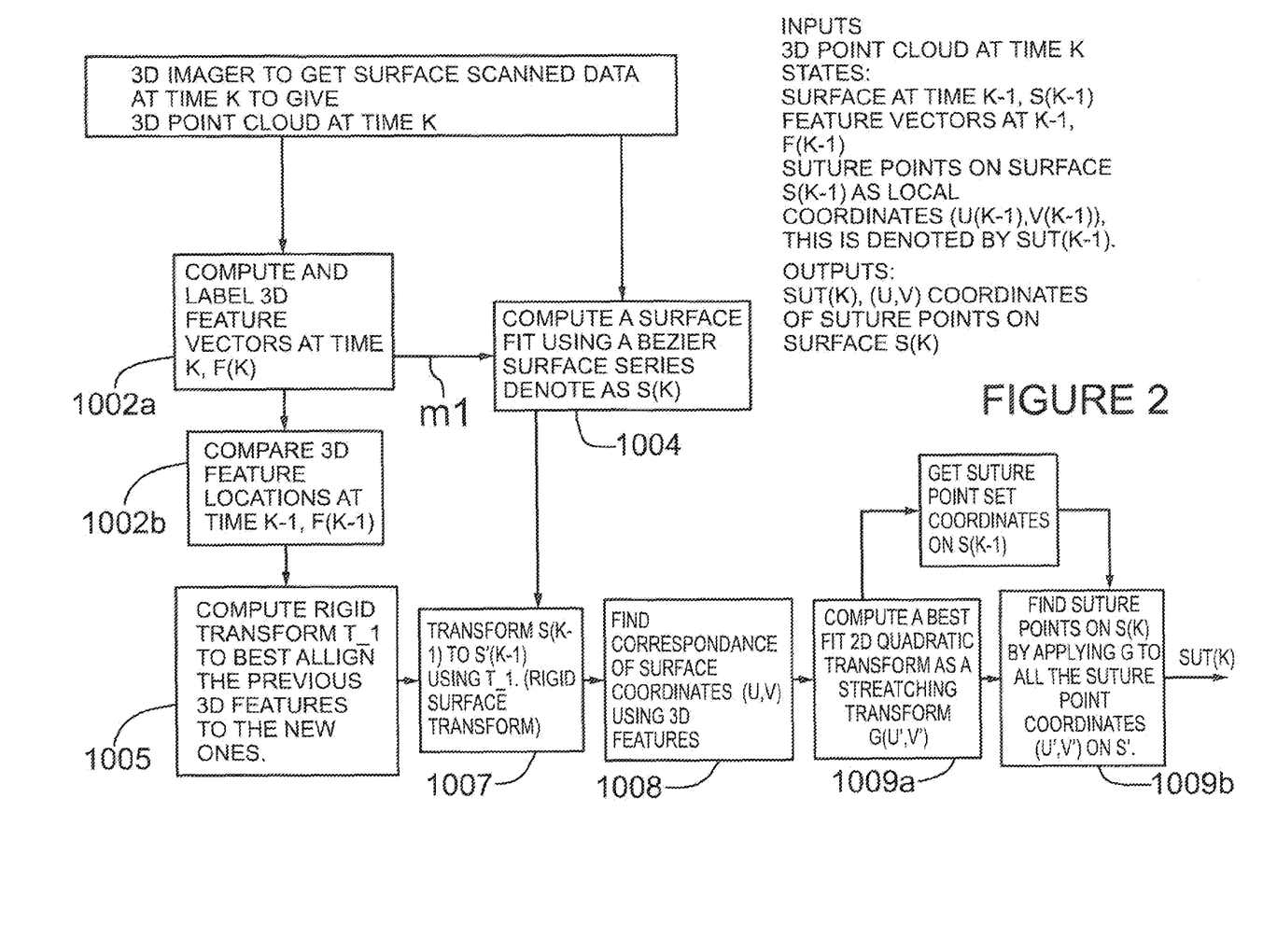
FIG. 2 shows a data flow/block diagram showing the steps for real-time tracking of moving and/or deforming surfaces using a direct 3D sensor.

While the embodiment described above for real-time tracking of moving surfaces included steps 1000*a*, 1000*b*, 1001*a*, 1001*b* and 1003 because a stereo camera was used, it will be understood that these steps could be replaced with another step if the stereo camera is replaced by some other device the output of which is a 3D point cloud of the moving surface at time K. Such devices include but are not limited to Lidar ((Light detection and ranging sensor), flash Lidar, in which the output is a 3D point cloud. FIG. 2 shows a flow diagram for this embodiment of the method of tracking moving surfaces.

To start the process, at time K=0 before tracking of the moving surface starts, a set of tracking points in the region of interest are transmitted to the vision processor programmed with the real-time tracking algorithm. Also at K=0, this vision processor computes a set of 3D SIFT feature vectors and a best fit surface from the dense stereo data. It maps the tracking points on the surface and stores this in the computer memory. At time K=1, new SIFT feature vectors and a best fit surface are computed from images recorded at time K=1 and these are used with the surface and the feature vectors stored at time K=0 to perform feature matching and the computation of the stretching transformation.

In addition to the real-time tracking method discussed above, the present invention provides a surgical system that includes a vision processor that executes the real-time tracking discussed above, a surgical robotic system which includes robotic hardware, various surgical tools, control software and an operator control interface required to perform various robotic assisted surgeries including but not limited to laparoscopic or catheter based anastomosis. The present surgical system relieves the surgeon of this complex manual task by performing selected steps in an automated fashion. The surgeon directs the robotic device via the operator control interface that which uses a vision system as shown and described in FIG. 1 or 2 which are coupled to the real-time tracking software used to implement the methods shown in FIG. 1 or 2. In this manner, the surgical procedure is performed by the robotic device, but directed by a comfortably seated surgeon who is immersed in the procedure via real time imagery through the real-time tracking provided by the vision processor.

Figure 3:
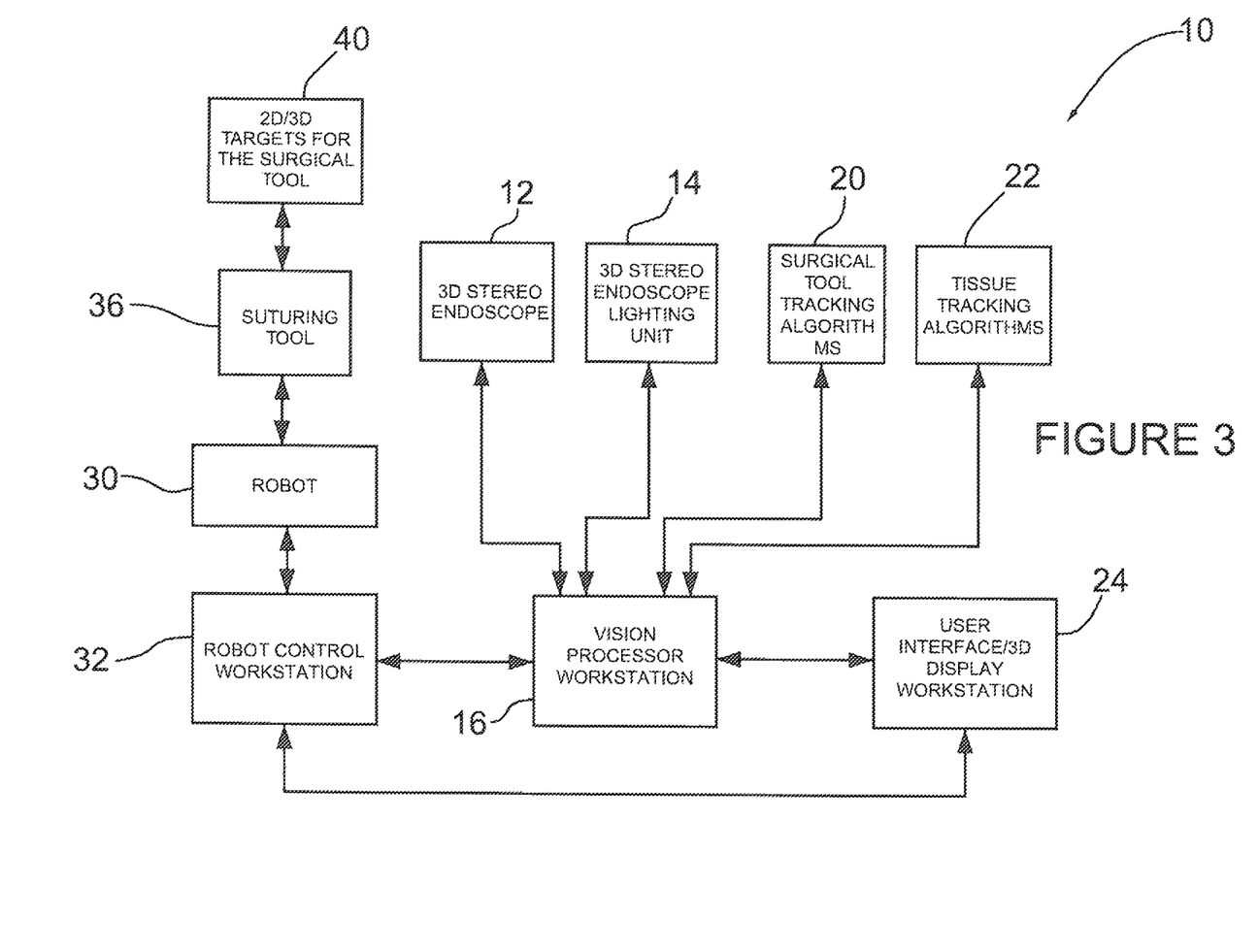
FIG. 3 shows a schematic block drawing showing the hardware/software blocks of a robotic surgical system using the methods of FIG. 1 or 2.

FIG. 3 is a schematic block drawing showing hardware/software blocks of the shared control image guided surgical system at 10. System 10 includes a stereo endoscope 12 which is capable of determining range data of physical bodies and surfaces in the surgical workspace. Stereo endoscope 12 includes left and right camera elements for taking left and right images of the same location. An endoscopic light unit 14 capable of illuminating the surgical workspace and also applying light of varying wavelength and potentially projecting patterns onto the tissue being operated on. Stereo endoscope 12 and endoscopic light unit 14 are interfaced with a vision processing system 16 which is programmed with standard surgical tool tracking and 3D model matching algorithms 20 in FIG. 3 and the tissue tracking algorithms 22 for which the flow diagrams are shown in FIG. 1 or 2 discussed above to determine the position of static and moving features and objects (e.g. lumen, desired suture points) within the surgical field. Vision processor 16 is programmed with algorithms to control the stereo endoscope image acquisition and the light source 14. The vision processor system 16 is interfaced with an operator control workstation 24 which displays the surgical field in 2D/3D and displays the updated regions of interest on the tissue surface such as updated suture positions computed in the vision processor system 16.

The surgical tool tracking algorithms 20 tracks the surgical tool 36 in the stereo endoscope images and outputs the surgical tool's 6 degrees of freedom pose (position and orientation) in the reference frame of the stereo endoscope 12. In one embodiment this includes placing a miniature 3D marker similar to the one proposed by Bondy et al. (Bondy, M., Krishnasamy, R., Crymble, D., and Jasiobedzki, P. (2007), *Space Vision Marker System, In Proceedings of AIAA SPACE Conference*) on the surgical tool and determining the position and orientation of the surgical tool 36 by matching the image features to the 3D model of the 3D marker. In another embodiment this includes directly matching the image features to a 3D computer aided design model of the surgical tool 36 without placing any markers. Alternatively, both methods may be used together to increase the robustness of the system wherein the 3D miniature marker can be used to provide an initial pose, subsequently, the change of surgical tool pose is tracked by matching the 3D model with the image of the surgical tool.

The vision processor workstation 16 may be programmed with an algorithm to reject outliers which are outside the allowable range of locations for the surgical tool 36. This algorithm performs smoothing to remove noise due to calibration and measurement errors in the estimated surgical tool pose. It is implemented as a standard filter with selectable parameters to optimize system performance.

The vision processor 16 may include algorithms to organize the image primitives into closed contours, open contours, regions corresponding to different anatomical structures and to compute various properties such as contour length and region area. This real time function converts the contour types into a feature vector. This feature vector may be used in steps 1001a and 1001b in addition to SIFT features to increase the robustness of the system when there are spurious features are in the image, or there are not enough SIFT features in an image.

The vision processor workstation 16 may be programmed with an algorithm to compute the deformation transformation of 2D closed contours on the moving surface. This function is used for contours that are visible all the time and always closed. If a contour becomes occluded, or is not entirely in the image, this algorithm tracks its deformation from frame to frame. This algorithm is discussed by Sharon and Mumford (Sharon, E., and David Bryant Mumford. 2006. 2D-shape analysis using conformal mapping. *International Journal of Computer Vision* 70 (1): 55-75.).

The vision processor workstation 16 is programmed with algorithms to select a next best viewing endoscope location (position and orientation). This algorithm selects the next best viewing location for the endoscope 12. In one configuration the endoscope 12 is positioned manually. In this case, the preferred location is shown on the visual display on the user interface display workstation 24 and feedback information is provided in the user display workstation 24 to assist manual positioning of endoscope 12. In another configuration, the endoscope 12 is mounted on a robotic positioner (not shown) and the endoscope 12 is moved to the next viewing location via commands to the robotic positioner.

A robotic surgical manipulator 30 is connected to a surgical robot controller 32 which in turn is connected to the vision processor system 16 and the operator control workstation 24, Surgical manipulator 30 includes an end effector which can releasibly grip various surgical tools 36, such as but not limited to suturing tools, stapling tools or tissue welders, to mention a few.

The system includes 2D/3D targets for different surgical tools 40. The 2D and 3D targets 40 are either passive or active targets which may be attached to the surgical tools 36.

In operation, for suturing applications of the present system, the operator control workstation 24 sends the suture points selected by the user to the vision processor workstation 16. Also operator control workstation 24 initiates the tracking algorithms 20 and 22 running on vision processor workstation 16. In addition, operator control workstation 24 receives telemetry data from the vision processor 16 and robot control workstation 32. The vision processor workstation 16 sends updated suture point locations to the robot control workstation 32 which in turn moves the surgical tool 36 to the updated suture point locations in a pre-selected order.

To start the process, at time K=0 before tracking of the moving tissue starts, the surgeon provides a set of tracking points which are transmitted to the vision processor workstation 16. Also at K=0, the vision processor 16 computes a set of 3D SIFT feature vectors and a best fit surface from the dense stereo data. It maps the tracking points on the surface and stores this in the computer memory. At time K=1, new SIFT feature vectors and a best fit surface are computed from images recorded at time K=1 and these are used with the surface and the feature vectors stored at time K=0 to perform feature matching and the computation of the stretching transformation.

The use of the above-described real-time tracking algorithms and robotic surgical system in various modes will now be described.

Method 1: Shared Control Anastomosis with Significant Surgeon Interaction

In this method, there is significant surgeon involvement. Specifically, this method of computer assisted anastomosis includes the following steps. First, images are acquired by the vision processor 16 and displayed at the operator control workstation 24. The sensing device for acquiring the images may be a 3D stereo endoscope 12 or as discussed above it may be a time-of-flight flash lidar, or a laser scanner to mention a few. The output data is a set of 3D coordinates of the tissue structures within the endoscope 12 field of view.

Second, the surgeon picks a point of interest to be operated on in the displayed image in the user interfaced display workstation 24 using an input device. The input device may be for example a cursor activated input device such provided by 2D mouse. The displayed images may be 2D or 3D images of the tissue being operated on, for example it may be anastomosis procedure joining two sections of lumen.

Thirdly, the robotic manipulator 30 brings the surgical tool 36 to a pre-defined position and then moves the tool tip of the surgical tool to the selected suture point by visual servoing to the selected feature on the lumen.

In the fourth step, the robotic control workstation 32 then sends commands to the surgical tool actuators to puncture the tissue at the specified suture point and pulls the suture through the pierced tissue. Once this action is completed the system backs off the surgical tool to a pre-defined position. Steps 1 to 4 are then repeated for the next suture point to perform a running suture.

In step six, the surgeon interacts directly with the robotic manipulator 30 in a tele-operated mode with a robot hand controller specifying the tool tip position and orientation, whereby the surgeon ties the final knot through commands to this hand controller (not shown) (e.g. haptic input device) in this shared control mode.

Variations on this process which add further flexibility and robustness are described in the following subsections.

Method 2: Alternate Means of Manual Specifying Suture Points by a Marking Device In this variation of the method, instead of the surgeon specifying the suture point on the 2D image, the surgeon manually marks a suture point on the lumen using a marking device. A physical marker such as a fluorescent marker integrated with the surgical tool 14 may be used to manually mark the suture point on the lumen.

Method 3: Manual Specification of Multiple Suture Points

In yet another variation of Method 1, the surgeon selects multiple suture points from the displayed images at once, different from Method 1 above where he picks one at a time. The multiple selected points are then tracked together and semi-autonomous suturing is performed with surgeon's supervision where the suture points are engaged in a selected order from a first designated suture point to a final suture point.

As noted earlier, while the real time tracking method disclosed herein is very useful for robotic assisted surgery, this method is generally applicable to real time tracking of any flexible/deformable moving surface.

As used herein, the terms "comprises", "comprising", "including" and "includes" are to be construed as being inclusive and open-ended. Specifically, when used in this document, the terms "comprises", "comprising", "including", "includes" and variations thereof, mean the specified features, steps or components are included in the described invention. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A vision system for real-time tracking of moving and flexible surfaces, comprising:
   a) a stereo endoscope for acquiring images of a region of a moving flexible surface, and a light source for illuminating the region of moving flexible surface;
   b) a vision processor connected to said stereo endoscope and said light source, said visional processor programmed with instructions for analyzing images from said stereo endoscope and computing, in real time, a current location of the region of moving flexible surface based on a current image of the region of moving flexible surface and a previous location of the region of moving flexible surface;
   c) a computer controller connected to said vision processor, said computer controller including a visual display for displaying images of a region of the moving flexible surface;
   d) said computer controller being programmed to pass one or more designated positions on said moving flexible surface to said vision processor, and wherein the vision processor is programmed to continuously track the one or more designated surgical positions on the moving flexible surface to provide updated positions of said one or more designated positions.

2. The system according to claim 1 wherein said vision processor is programmed for computing rigid and stretching transformations by the steps of
   a) synchronously acquiring left and right image frames from left and right camera members of a stereo camera, of the region of moving tissue at a time K;
   b) computing, from said left and right image frames 3D point cloud data in a coordinate frame of said stereo camera at said time K;
   c) fitting a parametric surface to said 3D point cloud at said time K;
   d) extracting a location of at least three features of interest in said left image frame at said time K in 2D pixel coordinates, extracting a location of each at least three feature of interest in said right image frame at said time K in 2D pixel coordinates, storing said 2D pixel coordinates of said locations of said features of interest in said left and right image frames at said time K in a vision processor memory storage;
   e) computing, using said stored 2D pixel coordinates of said locations of said features of interest in said left and right image frames at said time K, a 3D location of said features of interest at said time K in a coordinate frame of said camera and storing said 3D locations in said vision processor memory storage;

f) mapping said 3D location of said features of interest onto said parametric surface at time K and storing the parametric surface with mapped 3D locations in the vision processor memory storage;

g) retrieving from the vision processor memory storage 3D locations of said features of interest from previous left and right image frames synchronously taken at a time K−1;

h) computing said rigid transform using said retrieved 3D locations of the features of interest at time K−1 and the 3D locations of the features at time K;

i) retrieving from the vision processor memory storage a parametric surface with mapped 3D locations at time K−1, applying said rigid transformation to said retrieved parametric surface with mapped 3D locations at time K−1 to obtain an intermediate parametric surface with mapped 3D locations;

j) matching the 3D locations of features of interest on the intermediate parametric surface at time K−1 to the same corresponding 3D locations on the stored parametric surface at time K and from said correspondences computing said stretching transformation; and k) using said rigid and stretching transformations to calculate at time K a location of the region of moving tissue based on a location of the same region of moving tissue on said moving tissue at time K−1 stored in said vision processor memory storage.

3. An image-guided surgical system for performing procedures on deformable and/or moving sections of tissue, comprising:

a) a stereo endoscope for acquiring images of a region of moving tissue and a surgical tool tip being used in said region of tissue, and a light source for illuminating the region of moving tissue and said surgical tool;

b) a vision processor connected to said stereo endoscope and said light source, said visional processor programmed with instructions for analyzing images from said stereo endoscope and computing, in real time, a current location of the region of moving tissue based on a current image of the region of moving tissue and a previous location of the region of moving tissue;

c) a computer controller connected to said vision processor, said computer controller including a visual display for displaying images of a region of tissue being operated on in which the region of moving tissue is located;

d) a robot controller connected to said computer controller;

e) at least one surgical robot connected to said robot controller;

f) a surgical tool releasibly grippable by said robot, said surgical tool including said surgical tool tip;

g) said computer controller being programmed to pass one or more designated surgical positions being acted on by the surgical tool tip on the region of moving tissue to said vision processor, and wherein an operator initiates a surgical procedure by instructing the computer controller to command the robot to activate the surgical tool tip to proceed to a first of said one or more designated surgical positions, and wherein the vision processor is programmed to continuously track the one or more designated surgical positions on the moving tissue to provide updated positions of said one or more designated positions, and communicate these updated positions to said robot controller for tracking and to said computer controller for display to the operator, and wherein said computer controller is programmed to command said surgical robot to proceed to each designated position and perform a surgical procedure in a preselected order from the first designated position point to a final designated position.

4. The system according to claim 3 wherein said vision processor is programmed for computing rigid and stretching transformations to calculate at a current time K a location of any region on said moving tissue based on a location of the same region on said moving surface at previous time K−1.

5. The system according to claim 4 wherein said vision processor is programmed for computing rigid and stretching transformations by the steps of a) synchronously acquiring left and right image frames from left and right camera members of a stereo camera, of the region of moving tissue at a time K;

b) computing, from said left and right image frames 3D point cloud data in a coordinate frame of said stereo camera at said time K;

c) fitting a parametric surface to said 3D point cloud at said time K;

d) extracting a location of at least three features of interest in said left image frame at said time K in 2D pixel coordinates, extracting a location of each at least three feature of interest in said right image frame at said time K in 2D pixel coordinates, storing said 2D pixel coordinates of said locations of said features of interest in said left and right image frames at said time K in a vision processor memory storage;

e) computing, using said stored 2D pixel coordinates of said locations of said features of interest in said left and right image frames at said time K, a 3D location of said features of interest at said time K in a coordinate frame of said camera and storing said 3D locations in said vision processor memory storage;

f) mapping said 3D location of said features of interest onto said parametric surface at time K and storing the parametric surface with mapped 3D locations in the vision processor memory storage;

g) retrieving from the vision processor memory storage 3D locations of said features of interest from previous left and right image frames synchronously taken at a time K−1;

h) computing said rigid transform using said retrieved 3D locations of the features of interest at time K−1 and the 3D locations of the features at time K;

i) retrieving from the vision processor memory storage a parametric surface with mapped 3D locations at time K−1, applying said rigid transformation to said retrieved parametric surface with mapped 3D locations at time K−1 to obtain an intermediate parametric surface with mapped 3D locations;

j) matching the 3D locations of features of interest on the intermediate parametric surface at time K−1 to the same corresponding 3D locations on the stored parametric surface at time K and from said correspondences computing said stretching transformation; and k) using said rigid and stretching transformations to calculate at time K a location of the region of moving tissue based on a location of the same region of moving tissue on said moving tissue at time K−1 stored in said vision processor memory storage.

6. The system according to claim 3 wherein said one or more designated surgical positions are suture points.

7. The system according to claim 6 wherein said suture points are selected by an operator designating selected suture points on said left or right images.

8. The system according to claim 3 wherein said tissue is a deformable lumen.

9. The system according to claim 3 including a user operated input specification device for the operator to highlight said or more designated surgical positions being acted on by the surgical tool tip in the region of tissue being operated on.

10. The system according to claim 9 wherein said user operated input specification device is a software based cursor designation system configured such that an operator designates said one or more designated surgical positions on one or more of the displayed images of the region of tissue being operated on.

11. The system according to claim 9 wherein said user operated input specification device is a physical designation system configured such that an operator manually designates said one or more designated surgical positions directly on the region of tissue being operated on, and wherein said computer controller transmits coordinates of said one or more designated surgical positions to said surgical robot based on locations of said one or more designated surgical positions in a field of view of said stereo endoscope.

* * * * *